United States Patent [19]

Sharif

[11] Patent Number: 5,233,065

[45] Date of Patent: Aug. 3, 1993

[54] METHOD OF PREPARING STABLE ALUMINUM ACETATE SOLUTIONS

[75] Inventor: Sharif Sharif, Midland, Tex.

[73] Assignee: Zirconium Technology Corporation, Midland, Tex.

[21] Appl. No.: 912,289

[22] Filed: Jul. 13, 1992

[51] Int. Cl.$^5$ .............................................. C07F 5/06
[52] U.S. Cl. ................................................... 556/183
[58] Field of Search ......................................... 556/183

[56] References Cited

U.S. PATENT DOCUMENTS

| | | | |
|---|---|---|---|
| 2,086,499 | 7/1937 | Hennig | 260/11 |
| 2,306,826 | 12/1942 | Mendelsohn | 260/448 |
| 4,447,364 | 5/1984 | Staal | 260/448 R |
| 4,560,783 | 12/1985 | Shioyama et al. | 556/183 |

*Primary Examiner*—Jose' G. Dees
*Assistant Examiner*—Porfirio Nazario-Gonzalez
*Attorney, Agent, or Firm*—Robert C. Peterson

[57] ABSTRACT

This invention concerns the utilization of salts of alpha hydroxy carboxylic acids as stabilizers toward aging, boiling and dilution of aqueous aluminum acetate solutions. It also utilizes basic aluminum halides, other than fluorides, having the formula $Al_2(OH)_{6-m}Cl_m$ where $m = 1-5$ or the formula $Al(OH)_{3-n}Cl_n$ where $n = 1-2$, as starting aluminum raw material. The produced solutions are basic aluminum acetates with a pH that ranges from 2.0–7.0.

20 Claims, No Drawings

METHOD OF PREPARING STABLE ALUMINUM ACETATE SOLUTIONS

BACKGROUND OF THE INVENTION

1. Field of the Invention

The Field of the Invention is method of making aqueous aluminum acetate solution which is stable on boiling, heating and aging.

Aluminum acetate solutions are generally unstable and gradually decompose. With the decomposition product settling down in the solution in the form of sediment or deposit.

To avoid these problems, one patent, U.S. Pat. No. 2,306,826 describes a method of reacting in the solid state aluminum chloride and sodium acetate to form a neutral aluminum acetate which is completely water soluble in the solid form.

Another process described in U.S. Pat. No. 2,086,499 suggests that the evaporation of more than ⅓ basic aluminum acetate solutions operate to prepare finely crystalline products which are readily soluble and may be stored as aluminum acetate in the solid state for long stability.

U.S. Pat. No. 4,447,364, a process for preparing aluminum citrate complex describes in which an aqueous solution of aluminum trichloride containing up to 34% by weight $AlCl_3$ is combined with an aqueous solution of citric acid containing up to about 50% by weight citric acid. Thereafter a basic hydroxide in the form of an alkali metal or ammonium cation is added to the aluminum citrate solution to raise the pH between 5.5 and 7.5.

SUMMARY OF THE INVENTION

In Applicant's process a basic aluminum chloride having the formula $Al_2(OH)_{6-m}Cl_m$ where m=1-5 or the formula $Al(OH)_{3-n}Cl_n$ where n=1-2 are used. Furthermore, all basic aluminum halides other than fluorides may be used in the process.

Applicant has discovered a new method for the preparation of a very stable solution of aluminum acetate with aluminum concentrations as high as 22% $Al_2O_3$ by weight. The product is stable with aging, boiling and/or dilution.

In Applicant's process, 0.1-1.0 mols of acetic acid is added to 1 mol of the basic aluminum halide with adequate mixing. Best results and process feasibility are obtained when the basic aluminum halide solutions are adequately mixed during the addition of the glacial acetic acid. The addition of the glacial acetic acid causes the formation of white precipitate which is believed to be basic aluminum acetate. The precipitate redissolves soon after its formation. After all the glacial acetic acid has been added, the batch is then mixed for a period of time until a clear solution is obtained (usually 30 minutes, and in some cases with very large batches one hour). Next, while still mixing add alpha hydroxy carboxylic acid salt having a neutral to mildly alkaline (7-10) pH is added in concentrations of 2-20% by weight of alpha hydroxy carboxylic acid salt in the final solution, such as sodium, ammonium, potassium, or triethanolamine lactates, citrates or tartrates, or mixtures thereof, is added and mixing of the solution continues until a uniform clear solution is obtained. The final solution contains aluminum as aluminum trioxide in concentrations of 1-22% by weight with a preferred range of 10-20% by weight.

The alpha hydroxy carboxylic salt provides partial chelate bonding of the aluminum acetate which renders the solution stable. The process is illustrated by the following examples. The final solutions have a pH range from 2.0-7.0.

EXAMPLE 1

Preparation of Aluminum Acetate Solution

| COMPONENTS: | % BY WEIGHT | gms |
|---|---|---|
| 5/6 Basic Aluminum Chloride | 84.37% | 831.0 |
| Glacial Acetic Acid | 8.33% | 82.0 |
| 70.70% by wt. Sodium Lactate | 7.30% | 72.0 |
| | 100.00% | 985.0 |

PROCEDURE:
1) 82 mg of glacial acetic acid was gradually added to 831 gm of 5/6 basic aluminum chloride solution which contains 12.44% Al(23.5% as $Al_2O_3$) by weight.
2) After all of the glacial acetic acid was added, the batch was mixed until a clear solution was obtained (approximately 30 minutes).
3) While still mixing, 72 gm of 70.7% sodium lactate solution were added and agitation was continued until a uniform, clear solution was obtained.

The final product was aluminum acetate in solution with sodium lactate and the pH of the final solution from the preparation was 3.8 and it contained 16.3% $Al_2O_3$ (8.6% as Al) by weight.

EXAMPLE 2

Preparation of Aluminum Acetate Solution

In Examples 2-5, a solution called KA-1C is used. The KA-1C is a solution of 45% by weight of 50% sodium hydroxide solution and 55% by weight of an 88% lactic acid solution.

| COMPONENTS: | % BY WEIGHT |
|---|---|
| 50% 5/6 Basic Aluminum Chloride | 78.40% |
| Glacial Acetic Acid | 7.78% |
| KA-1C | 13.82% |
| | 100.00% |

PROCEDURE:
1) Dissolve the glacial acetic acid in the chlorhydrol solution. Mix with high agitation and add the acetic acid slowly as this reaction occurs in a relatively slow manner.
2) Add the KA-1C to the above solution slowly. Mix for a minimum of 30 minutes.
3) Check for clarity of the product.

The final product was aluminum acetate in solution with sodium lactate. The pH of the final solution was 3.6. The solution contained 18.4% by weight Al as $Al_2O_3$.

EXAMPLE 3

Preparation of Aluminum Acetate Solution

| COMPONENTS: | % BY WEIGHT |
|---|---|
| 50% 5/6 Basic Aluminum Chloride | 69.15% |
| Glacial Acetic Acid | 6.85% |
| KA-1C (same as Ex. 2) | 24.00% |
| | 100.00% |

PROCEDURE:
1) Dissolve the glacial acetic acid in the 50% 5/6 basic aluminum chloride. Mix with high agitation and add the -continued acetic acid slowly as this reaction occurs in a
relatively slow manner.
2) Add the KA-1C to the above solution slowly. Mix for
a minimum of 30 minutes or until product is clear.

The final product was aluminum acetate in solution with sodium lactate. The pH of the final solution was 3.5. The solution contained 16.3% by weight Al as $Al_2O_3$.

EXAMPLE 4 Preparation of Aluminum Acetate Solution From ⅓ Basic Aluminum Chloride

| COMPONENTS: | % BY WEIGHT | gms |
|---|---|---|
| D.I. water | 6.92% | 50.0 |
| 1/3 Basic Aluminum Chloride | 55.72% | 402.7 |
| Glacial Acetic Acide | 9.55% | 69.0 |
| KA-1C (same as Ex. 2) | 27.81% | 201.0 |
| | 100.00% | 722.7 |

PROCUDURE:

1) Add 50 gm of D.I. water to 402.7 gm of 1/3 basic aluminum chloride which contains 13.7% $Al_2O_3$. Mix for 5 minutes.
2) While mixing, add 69.0 gm of glacial acetic acid and continue mixing for 15 minutes.
3) Add 201.0 gm of KA-1C and mix for 15 minutes. Clear and stable solution was obtained.

The final product was aluminum acetate in solution with sodium lactate. The pH of the final solution was 2.9. The solution contained 7.5% by weight of Al as $Al_2O_3$.

EXAMPLE 5 Preparation of Aluminum Acetate Solution From ⅔ Basic Aluminum Chloride

| COMPONENTS: | % BY WEIGHT | gms |
|---|---|---|
| 2/3 Basic Aluminum Chloride | 75.96% | 200.0 |
| Glacial Acetic Acid | 5.55% | 14.8 |
| KA-1C (same as Ex. 2) | 19.49% | 52.0 |
| | 100.00% | 266.8 |

PROCEDURE:

1) While mixing, add 14.8 gm of glacial acetic acid to 200 gm of 2/3 basic aluminum chloride which contains 17.6% $Al_2O_3$.
2) Mix for 15 minutes.
3) Add 52.0 gm of KA-1C and mix for 15 minutes. A stable and clear solution was obtained.

The final product was aluminum acetate in solution with sodium lactate. The pH of the final solution was 3.1. The solution contained 13.2% by weight Al as $Al_2O_3$.

It should be appreciated that the alpha hydroxy carboxylic acid salts may be utilized in the process to produce stable aluminum acetate solutions or otherwise act as stabilizers through partial chelation bonding. The following salts of alpha hydroxy carboxylic acids can be used as stabilizers of aluminum acetate solutions:

Sodium Zirconium Tartrate
Sodium Zirconium Glycolate
Sodium Zirconium Maliate
Sodium Zirconium Saccharate
Sodium Zirconium Gluconate
Sodium Zirconium Glycerate
Sodium Zirconium Mandelate
Ammonium Zirconium Citrate
Ammonium Zirconium Tartrate
Ammonium Zirconium Glycolate
Ammonium Zirconium Maliate
Ammonium Zirconium Saccharate
Ammonium Zirconium Gluconate
Ammonium Zirconium Glycerate
Ammonium Zirconium Mandelate
Potassium Zirconium Lactate
Potassium Zirconium Citrate
Potassium Zirconium Glycolate
Potassium Zirconium Maliate
Potassium Zirconium Saccharate
Potassium Zirconium Gluconate
Potassium Zirconium Glycerate
Potassium Zirconium Mandelate
Amine (or amine derivative) Zirconium Citrate
Amine (or amine derivative) Zirconium Tartrate
Amine (or amine derivative) Zirconium Glycolate
Amine (or amine derivative) Zirconium Maliate
Amine (or amine derivative) Zirconium Saccharate
Amine (or amine derivative) Zirconium Gluconate
Amine (or amine derivative) Zirconium Glycerate
Amine (or amine derivative) Zirconium Mandelate

What is claimed is:

1. The method of preparing a stable aluminum acetate solution comprising the following steps:

Adding 0.1–1.0 mols acetic acid to 1 mol of basic aluminum chloride having the formula:
   $Al(OH)_{3-n}Cl_n$ where n=1–2, and/or
   $Al_2(OH)_{6-m}Cl_m$ where m=1–5,
   Permitting the reaction to continue with mixing until a clear solution is obtained,
   Add, while still mixing, an alpha hydroxy carboxylic acid salt selected from the group consisting of sodium, ammonium, potassium and triethanolamine lactates, citrates or tartrates, or mixtures thereof, and Continue mixing until a clear solution is obtained.

2. The method of claim 1 wherein the concentration of aluminum as $Al_2O_3$ is 1–22% by weight in the final solution.

3. The method of claim 1 wherein the concentration of aluminum as $Al_2O_3$ is 10–20% by weight in the final solution.

4. The method of claim 2 wherein the concentration of the alpha hydroxy carboxylic acid salt is 2–20% by weight in the final solution.

5. The method of claim 4 wherein the pH of the alpha hydroxy carboxylic acid salt is 7–10.

6. The method of preparing a stable aluminum acetate solution comprising the following steps:

Adding 0.1–1.0 mols of acetic acid to 1 mol of a solution of basic aluminum halide, having the formula:
   $Al(OH)_{3-n}X_n$ where n=1–2, and/or
   $Al_2(OH)_{6-m}Y_m$, where m=1–5,
   and where X and Y are selected from the group consisting of iodine, bromine and chlorine,
   Mixing the reactants until a clear solution is obtained,
   Adding alpha hydroxy carboxylic acid salt selected from the group consisting of sodium, ammonium, potassium, triethanolamine lactates, citrates or tartrates, or mixtures thereof, and
   Continue mixing until a clear solution is obtained.

7. The method of claim 6 wherein X and Y are chlorine.

8. The method of claim 6 wherein X and Y are bromine.

9. The method of claim 6 wherein X and Y are iodine.

10. The method of claim 6 wherein the concentration of aluminum as $Al_2O_3$ is 1-22% by weight in the final solution.

11. The method of claim 6 wherein the concentration of aluminum as $Al_2O_3$ is 10-20% by weight in the final solution.

12. The method of claim 10 wherein the concentration of the alpha hydroxy carboxylic acid salt is 2-20% by weight in the final solution.

13. The method of claim 12 wherein the pH of the alpha hydroxy carboxylic acid salt is 7-10.

14. The method of claim 4 wherein the basic Aluminum chloride has the formula:
$Al(OH)_{3-n}Cl_n$ where $n=1$ 15. The method of claim 4 wherein the basic aluminum chloride has the formula:
$Al(OH)_{3-n}Cl_n$ where $n=2$ 16. The method of claim 4 wherein the basic aluminum chloride has the formula:
$Al_2(OH)_{6-m}Cl_m$ where $m=1$ 17. The method of claim 4 wherein the basic aluminum chloride has the formula:
$Al_2(OH)_{6-m}Cl_m$ where $m=2$ 18. The method of claim 4 wherein the basic aluminum chloride has the formula:
$Al_2(OH)_{6-m}Cl_m$ where $m=3$ 19. The method of claim 4 wherein the basic aluminum chloride has the formula:
$Al_2(OH)_{6-m}Cl_m$ where $m=4$ 20. The method of claim 4 wherein the basic aluminum chloride has the formula:
$Al_2(OH)_{6-m}Cl_m$ where $m=5$

* * * * *